United States Patent [19]

Bellattar et al.

[11] Patent Number: 4,736,019
[45] Date of Patent: Apr. 5, 1988

[54] PROCESS FOR THE SEPARATION OF ANTIFACTOR VIII:C ANTIBODIES, MORE PARTICULARLY USABLE FOR THE PURIFICATION OF THE BLOOD PLASMA OF A TYPE A HEMOPHILIAC

[75] Inventors: Noureddine Bellattar, Fontenay; Danielle Gulino, Neuilly-Plaisance; Jacqueline Jozefonvicz, Lamorlaye, all of France

[73] Assignee: Commissariat a l'Energie Atomique, Paris, France

[21] Appl. No.: 865,333

[22] Filed: May 21, 1986

[30] Foreign Application Priority Data

May 31, 1985 [FR] France ................. 85 08227

[51] Int. Cl.$^4$ ............ 601N 33/50; 601N 30/00; A61M 1/36
[52] U.S. Cl. ............................ 530/387; 530/383; 530/413; 530/415; 530/417; 530/811; 530/813; 530/815; 530/816; 424/85; 424/101; 525/54.1; 436/532; 435/181
[58] Field of Search ........... 530/383, 387, 412, 413, 530/415, 417, 811, 812, 813, 815, 816; 424/85, 101; 525/54.1, 54.11; 436/532; 435/181

[56] References Cited

U.S. PATENT DOCUMENTS 3,969,284  7/1976  Gray ..................... 525/54.1
4,569,967  2/1986  Kornreich et al. ......... 525/54.11

FOREIGN PATENT DOCUMENTS 2548193  4/1985  France.

OTHER PUBLICATIONS

Nilsson et al, "A Procedure for Removing High Titer Antibodies by Extracorporeal Protein-A-Sepharose Adsorption in Hemophilia! Substitution Therapy and Surgery in a Patient with Hemophilia B and Antibodies" *Blood*, vol. 58, No. 1 (Jul.) 1981, pp. 38–44.
Chemical Abstracts, vol. 91, ref 54 297z(1979).
Chemical Abstracts, vol. 101, ref 52 882n(1984).

*Primary Examiner*—Delbert R. Phillips
*Assistant Examiner*—Nathan M. Nutter
*Attorney, Agent, or Firm*—Oblon, Fisher, Spivak, McClelland & Maier

[57] ABSTRACT

The process for the separation of antiVIII:C antibodies present in a liquid consists of contacting said liquid with a solid support constituted by a polymer or a copolymer having in its chain substitutable groups, whereof at least part is substituted by groups having an affinity for antiVIII:C antibodies and a selectivity for antiVIII:C antibodies compared with other immunoglobulins and then separating the liquid from the support on which have been adsorbed the antiVIII:C antibodies.

Preferably use is made of polystyrene, to which have been fixed groups —$SO_3Na$ and —$SO_2Glu$, —$SO_2Threo$, —$SO_2OHPro$ or $SO_2Lys$. These supports can be used for ex-vivo purification in the column of the blood plasma of a type A hemophiliac.

13 Claims, 3 Drawing Sheets

PROCESS FOR THE SEPARATION OF ANTIFACTOR VIII:C ANTIBODIES, MORE PARTICULARLY USABLE FOR THE PURIFICATION OF THE BLOOD PLASMA OF A TYPE A HEMOPHILIAC

BACKGROUND OF THE INVENTION

The present invention relates to a process for the separation of anti VIII:C antibodies present in a liquid, such as blood plasma. More specifically, it relates to insoluble polymer or copolymer supports usable for the selective purification of the specific antibodies of factor VIII:C, i.e. the anti VIII:C antibodies present in the blood plasma, such as that of a patient suffering type A hemophilia. Thus, in the case of type A hemophiliacs who have had repeated blood transfusions, in general anti VIII:C antibodies form, which neutralize the coagulating activity of the transfused factor VIII:C. The presence of these antibodies leads to serious difficulties. Moreover, in order to treat hemorrhages in A type hemophiliacs, it is generally necessary to carry out exchanges of the blood plasma, immediately followed by VIII:C factor injections, in order to obtain a normal hemostasis and this treatment often has to be continued for a long time, as a function of the state of the patient. The leads to serious problems, because it is difficult under such conditions to maintain the indispensable constituents of the patient's blood plasma at the desired levels. Moreover, the risks of infection by viruses, such as that of hepatitis or LAV/HTLV3 virus become greater with the number of transfusions.

In addition, for some years now, research has aimed at processes for the direct purification of the plasma by the adsorption of disturbing elements on an appropriate support. In the case of B type hemophiliacs, it has been possible to carry out this purification by adsorption of specific antibodies factor IX, i.e. anti IX antibodies, on a protein A bonded by covalency to agarose, as is described by I. M. Nilsson et al in Blood, Vol 58, No 1 (July 1981), pp 38 to 44. The protein A reacts with the Fc part of the immunoglobulins and when it is bonded with sepharose, it can be used as an immunosorbent for isolating the immunoglobulins G and consequently the antifactor IX. However, the total immunoglobulin content of the thus treated plasma represent no more than 1/5 of its original value, which leads to certain problems. Furthermore, present research has been directed at immunosorbents able to selectively separate the desired antibodies, specifically those present in the blood of hemophiliacs.

In the case of antiVIII:C antibodies, present research has not made it possible to selectively and quantitatively separate these antibodies. Thus, consideration has been given to carrying out said separation by selective adsorption by means of a chromatographic gel on which is immobilized the VIII:C factor. However, this method is unusable, because the VIII:C factor very rapidly loses its antigen properties.

For several years now, research has been directed at the use of inert supports, to which are fixed appropriate compounds making it possible to give the support a particular affinity, e.g. for certain constituents of the blood. Thus, French patent No. 83/10773, filed on June 29, 1983 by the C.E.A, illustrates the use of polymers of this type for the separation and purification of thrombin. In this case, arginine, nitroarginine or one of the derivatives thereof, such as methyl ester is fixed to the polymer or copolymer for giving the support said affinity with respect to thrombin.

SUMMARY OF THE INVENTION

The present invention relates to a process for the separation of antiVIII:C antibodies present in a liquid by means of supports of the same type, which can be used for the plasma purification of the blood of type A hemophiliacs, because it makes it possible to selectively separate the antiVIII:C antibodies from the other immunoglobulins G.

The present invention therefore relates to a process for the separation of antiVIII:C antibodies present in a liquid, wherein it comprises:

(a) contacting said liquid with a solid support constituted by a polymer or copolymer having substitutable groups in its chain and whereof at least part is substituted by groups of formula $-(SO_3)_xM$, in which M represent a metal which does not react with the liquid and x represents the valency of M, and/or formula $-SO_2Y$ and/or formula $-COY$, in which Y represents a radical obtained by removing a hydrogen atom from the amino function of an α-amino acid other than arginine or an α-amino acid derivative other than arginine having an affinity for antiVIII:C antibodies and a selectivity for antiVIII:C antibodies with respect to other immunoglobulins and (b) then separating the liquid from the support on which have been adsorbed the antiVIII:C antibodies.

In order to obtain a good affinity and a good selectivity of the adsorbant for the antiVIII:C antibodies with respect to the other immunoglobulins, radical Y preferably complies with the following formula:

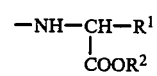

in which $R^1$ represents the side chain of an α-amino acid and $R^2$ represents a hydrogen atom or an alkyl radical e.g. having 1 to 5 carbon atoms, the $R^1$ radical having at least one function chosen from among the functions $COOH, -NH_2, -OH$ and $-SH$.

Examples of radicals Y which can be used are those obtained from glutamic acid, hydroxyproline, alanine, phenylalanine, threonine and lysine. Preferably, radical Y is a radical from glutamic acid, hydroxyproline, threonine or lysine.

According to the invention, when the α-amino acid, which is the precursor of the radical Y comprises several amino functions, the amine function of said α-amino acid or its derivative from which is removed a hydrogen atom for forming the radical Y is the amino function located at α.

According to the invention, groups $-SO_2Y$, $-(SO_3)_xM$ and/or $-COY$ can be fixed to the polymer via hydrocarbonated chains or groups, e.g. peptide chains in the case of COY groups.

According to the invention, the polymers and copolymers which can be used are solid materials having along their chain substitutable groups which can react with chlorosulphonic acid. Examples of such polymers are crosslinked polystyrene, cellulose esters, cellulose ethers, polyvinyl acetate, polyvinyl chloride, polyisoprene and polybutadiene. It is also possible to use copolymers of styrene, copolymers of vinyl acetate, copolymers of vinyl chloride, copolymers of isoprene and copolymers of butadiene. It is also pointed out that the term copolymer is also understood to mean grafted copolymers obtained by grafting a vinyl monomer on a basic polymer, e.g. styrene copolymers constituted by a chlorosulphonation-resistant polymer grafted by styrene. In this case, the chlorosulphonation-resistant basic polymer can be chosen from among polyolefins, fluorinated polymers and polyvinyl chloride.

Preferably, use is made of styrene or a styrene copolymer and in this case the groups fixed to the polymer or copolymer are generally of two types, on the one hand groups of formula $SO_2Y$, in which Y has the meaning given hereinbefore and on the other hand groups of formula $=(SO_3)_xM$, in which M represent a metal not reacting with the liquid and x represents the valence of the metal M, which is generally sodium.

The invention also applies to polymers and copolymers which can be carboxymethylated, e.g. polysaccharides such as polydextran.

The supports according to the invention in which the basic polymer is styrene or a styrene copolymer can be obtained by a process comprising a first stage of chlorosulphonating the polymer or copolymer by the reaction thereof with chlorosulphonic acid and a second stage consisting of transforming at least part of the groups —$SO_2Cl$ fixed to the polymer or copolymer into —$SO_2Y$ groups.

When using polystyrene, the chlorosulphonation reaction corresponds to the following reaction diagram:

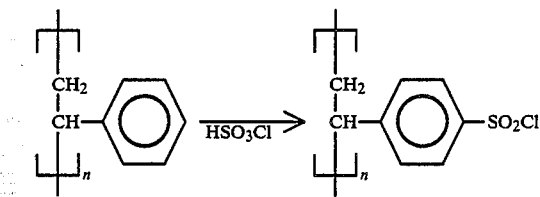

This reaction can be performed in an organic medium advantageously constituted by a chlorinated solvent, such as dichloromethane, to which nitromethane is added.

In the second stage, the chlorosulphonyl groups —$SO_2Cl$ are transformed into Y groups by reacting with the corresponding α-amino acid, which complies with the formula:

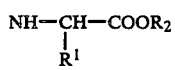

in which $R^1$ represents the side chain of the α-amino acid and $R^2$ represents a hydrogen atom or an alkyl radical. This reaction corresponds to the following reaction diagram:

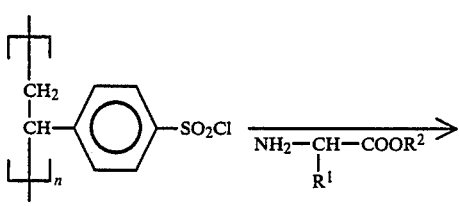

-continued

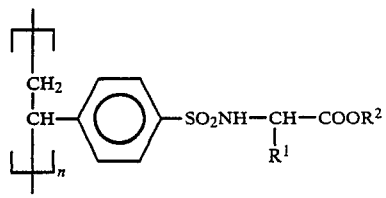

It is generally carried out in a medium containing the water - dioxane mixture at ambient temperature, when $R^2$ represents a hydrogen atom and in a medium containing dichloromethane at a temperature slightly above ambient temperature, when $R^2$ represents an alkyl radical.

In the case of polystyrene, at the end of the operation a material is obtained which has groups of the following formula:

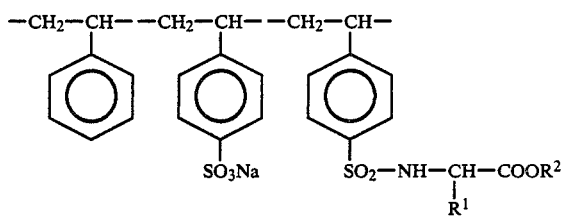

The number of groups substituted by —$SO_3Na$ and by

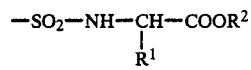

is in particular dependent on the reaction conditions. To obtain good results, it is preferable for the number of styrene groups substituted by groups —$SO_2Y$ or —COY to be between 10 and 30%.

The solid supports according to the invention constituted by a polymer or copolymer having groups of formula —COY can be obtained by a process having a first carboxymethylation, followed by a second stage of fixing an appropriate amine or benzyl chloride, a third stage of fixing the amino acid from which the radical Y is formed and a fourth sulphonation stage.

In this case, the polymer can be a polysaccharide, such as polydextran and the groups fixed to the basic polymer are not only groups of formula —COY, but also groups of formula $CH_2CONHR^4$—$SO_3R^5$, in which $R^4$ represents an alkyl, aryl or alkylaryl radical, which may or may not be substituted and $R^5$ represents a hydrogen atom or a metal not reacting with the liquid, such as sodium.

When use is made of a styrene copolymer support obtained by grafting styrene to a chlorosulphonation-resistant polymer, grafting preferably takes place by irradiation using ionizing rays. In this case, it is possible to submerge a chlorosulphonation-resistant polymer in a styrene solution and subject this to irradiation in an oxygen-free atmosphere, e.g. using as the radiation source a cobalt 60 source.

The grafting level of the powder is controlled by acting on the styrene concentration of the solution, on the type of solvent, on the diffusion time, on the total irradiation dose and on the irradiation dose rate. Following irradiation, the grafted product is generally washed, e.g. using styrene followed by alcohol and then it is dried.

This method of preparing the grafted powder is particularly advantageous, because it makes it possible to obtain a grafting of the styrene on the surface of the powder and give thereto, following the fixing of appropriate groups, a good affinity and a good selectivity for the antiVIII:C antibodies.

The process according to the invention can in particular be used for treating liquid constituted by blood plasma, especially blood plasma from type A hemophiliacs. In this case, it is possible to use the process according to the invention for the ex-vivo purification of the blood of patients of this type.

BRIEF DESCRIPTION OF THE DRAWINGS

The invention is described in greater detail hereinafter relative to non-limitative embodiments and the attached drawings, wherein show.

DETAILED DESCRIPTION OF THE INVENTION

EXAMPLE 1

Figure 1:
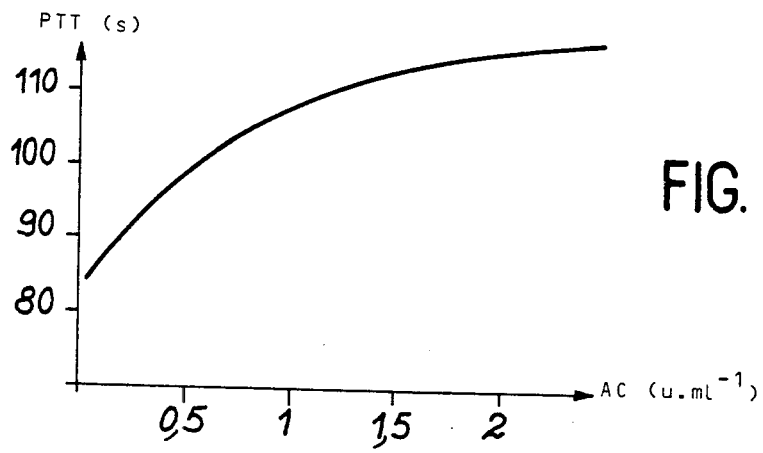
FIG. 1. the standard curve making it possible to determine the antiVIII:C antibody concentrations of samples on the basis of the partial thromboplastin times (PTT).

Preparation of a polystyrene support having —$SO_2$Glu and —$SO_3$NA groups (a) Preparation of chlorosulphonated polystyrene 18 g of crosslinked polystyrene balls having a grain size of 40 to 70 μm are allowed to swell for three hours at ambient temperature in 1440 ml of dichloromethane. The is followed by the addition of a mixture of 270 ml of dichloromethane and 227 ml of chlorosulphonic acid. The suspension is stirred for 25 minutes at ambient temperature, followed by the filtration of the crude resin. This is followed by careful washing with dichloromethane - dioxan mixtures, followed by drying in vacuo at 50° C.

The level of the chlorosulphonyl groups (—$SO_2$Cl) groups is then determined in the following way. 200 mg of chlorosulphonated polystyrene are hydrolized with 40 ml of a 1 M NaOH solution for 24 hours under reflux. Following acidification, the released Cl$^-$ ions are titrated by a 0.1 M $AgNo_3$ solution using a silver indicator electrode.

(b) FIXING GLUTAMIC ACID ON CHLOROSULPHONYL FUNCTIONS

A glutamic acid solution is prepared in a solvent constituted by a mixture of water and dioxan in a ratio of 3:2 and the pH of the solution is adjusted to 9/10 by adding 4 M soda for dissolving the glutamic acid. This is followed by the addition of 10 g of the previously obtained chlorosulphonated polystyrene and the pH is kept at its initial value of 9–10 by adding 2 M soda. The reaction is completed when the pH remains stable. The polymer is then filtered, washed abundantly with water, then with $10^{-2}$ M soda and then water, followed by drying in vacuo.

This is followed by the determination of the content of —$SO_2$Glu groups in the polymer obtained by elementary analysis of the nitrogen content. There is also a determination of of the content of $SO_3$Na groups from the content of the previously determined chlorosulphonyl groups and the content of —$SO_2$Glu groups. The results obtained are given in the attached table.

EXAMPLES 2 to 8

Preparation of polystyrene supports having groups —$SO_2$Ala, $SO_2$PheAla, —$SO_2$OHPro, —$SO_2$Threo, —$SO_2$Y with Y representing the radical derived from methyl glutamate —$SO_2$Pro or —$SO_2$Lys.

Use is made of chlorosulphonated polystyrene, like that obtained in example 1(a), followed by the fixing thereto of the amino acid or the corresponding amino acid derivative, namely alanine (example 2), phenylalanine (example 3), hydroxyproline (example 4), threonine (example 5), methyl glutamate (example 6), proline (example 7) or lysine (example 8) using the same operating procedure as in example 1(b). As hereinbefore, determination takes place of the contents of groups —$SO_2$Y and —$SO_3$Na of the thus obtained supports. The results are given in the attached table.

Example 9

This example illustrates the use of the supports of examples 1 to 8 for adsorbing the antiVIII:C antibodies present in the plasma of a hemophiliac.

(a) CONDITIONING AND WASHING SUPPORTS

The supports of examples 1 to 8 are firstly conditioned in order to completely eliminate any impurity, which could react with the proteins of the blood. This is followed by successive washing of the support with a 1.5 M sodium chloride solution and 1.0 M sodium citrate solutions. This support is then balanced in Michaelis buffer (pH 7.3), followed by filtration, washing several times with water and drying in vacuo. Following grinding, the mean dimensions of the particles of the water-swollen supports, determined using a TAS-type quantitative microscope are in the range 5 to 10 μm.

(b) PREPARATION OF SAMPLES

Firstly plasma samples are prepared, on the one hand from the blood of a hemophiliac having antiVIII:C antibodies and on the other hand from blood collected from 15 normal reference patients. The blood is collected on a 3.8% trisodium citrate solution, at a rate of one volume of citrate solution for nine volumes of blood, followed by storage at a temperature of −70° C.

This is followed by the isolation of the immunoglobulins of the plasma of the hemophiliac, whose antiVIII:C antibody titre in the plasma is 640 Bethesda units/ml. To this end, the plasma of the hemophiliac is defibrinated and then dialysed against a phosphate buffer (0.005 M, pH=6.5) for one night at 4° C.

The serum obtained is then passed on to a DEAE 52 cellulose column and the fraction containing immunoglobulins IgG are collected and then concentrated. They are then abundantly dialysed against a 0.15 M NaCl solution. The final preparation of immunoglobulins G from the hemophiliac (IgG$_H$) has an antiVIII:C antibody activity of Bethesda units/mg of IgG.

The antiVIII:C antibody concentration is determined according to the method described at the Bethesda conference by C. K. KASPER et al "A more uniform measurement of factor VIII inhibitors" Thromb. Diath. Haemorrh, Vol 34, p 869, 1975. According to this method, 0.1 ml of plasma concentration containing antiVIII:C or the preparation of IgG is incubated with 0.1 ml of normal plasma for two hours at 37° C. This is followed by the determination of the procoagulant activity of the VIII factor of the mixture and it is compared with that of a control tube in which the Michaelis buffer has been incubated with normal plasma. The procoagulant activity of factor VIII is measured on the basis of the partial thromboplastine time (PTT) using human plasma having a factor VIII deficiency as the substrate and normal plasma prepared in as described hereinbefore as the standard (1 u/ml). The antiVIII:C activity unit is defined as that which deactivates 50% of the procoagulant activity of the control sample during incubation for two hours. Thus, the antiVIII:C antibody concentration, expressed in Bethesda units is obtained by determining the inverse of the dilution rate of the control plasma preparation or the IgG preparation which deactivates 0.5 u of VIII:C during the two hours incubation.

(c) ADSORPTION TESTS

These tests are performed by incubating 50 ul of IgG$_H$ preparations at varied concentrations, either with a suspension of one of the supports of examples 1 to 7 using 2 to 10 mg/ml of support, or with the michaelis buffer. After incubating for 30 minutes, the mixtures containing EgG$_H$ are centrifuged and this is followed by the determination of the IgG and/or antiVIII:C antibody concentrations of the supernatants in the following way:

(1) the IgG concentration is measured by radial immunodiffusion using ICL plates (plates marketed by ICL Scientific, Fountain Valley, Calif.). The low or very low level dosage kits where used as a function of the IgG concentrations to be determined. In order to carry out the measurements, on the same plate are treated two standard samples having known IgG immunoglobulin concentrations, respectively 0.15 and 3 mg/ml, with four supernatants containing IgG$_H$ and in order to obtain a maximum reproducibility, use is made of an accurate micropipette able to supply a 5.0 ul supernatant volume to each means. Moreover, to prevent any distortion of the results, the samples corresponding to the IgG concentration before and after adsorption are supplied to two adjacent means.

(2) the quantitative antiVIII:C antibody determination is performed using a standard curve, which correlates the partial thromboplastin time (PTT) and the antiVIII:C antibody concentrations. This standard curve is obtained from IgG$_H$ preparations having antiVIII:C concentrations ranging from 0 to two bethesda units/ml, which are obtained by diluting the IgG$_H$ preparation. In order to establish the standard curve, the different IgG$_H$ dilutions containing antiVIII:C are incubated, firstly with normal plasma for two hours at 37° C. and then, following a 1/10 dilution, 0.1 ml of these mixtures is incubated with 0.1 ml of hemophilia plasma and 0.1 ml of cephalin activated for 10 minutes. The partial thromboplastin times (PTT) are then measured after adding 0.1 m of CaCl$_2$.

There is a PTT rise, as soon as the antiVIII:C concentration increases. The results obtained are given in the attached FIG. 1, which illustrates the standard curve obtained representing the PTT in seconds, as function of the antiVIII:C concentration in u/ml.

After establishing this standard curve, the partial thromboplastin times are measured on the supernatants and their antiVIII:C concentrations are determined using the standard curve and the dilution factors.

These different measurements make it possible to determine the initial IgG and antiVIII:C antibody concentrations of the samples before adsorption and the residual concentrations of IgG and antiVIII:C antibodies of the samples after their contacting with adsorbant supports.

Thus, the IgG and antiVIII:C concentrations of the samples, which where contacted with the Michaelis buffer respectively correspond to the initial concentrations divided by two in IgG and antiVIII:C of the samples. The IgG and antiVIII:C concentrations of the samples contacted with the adsorbant supports correspond to the residual IgG and antiVIII:C concentrations. Thus, it is possible to deduce therefrom the IgG and antiVIII:C antibody levels adsrobed on the different supports.

On the basis of the results obtained on different samples, it is possible to produce the isotherm adsorption curves of IgG and antiVIII:C antibodies.

Figure 2:
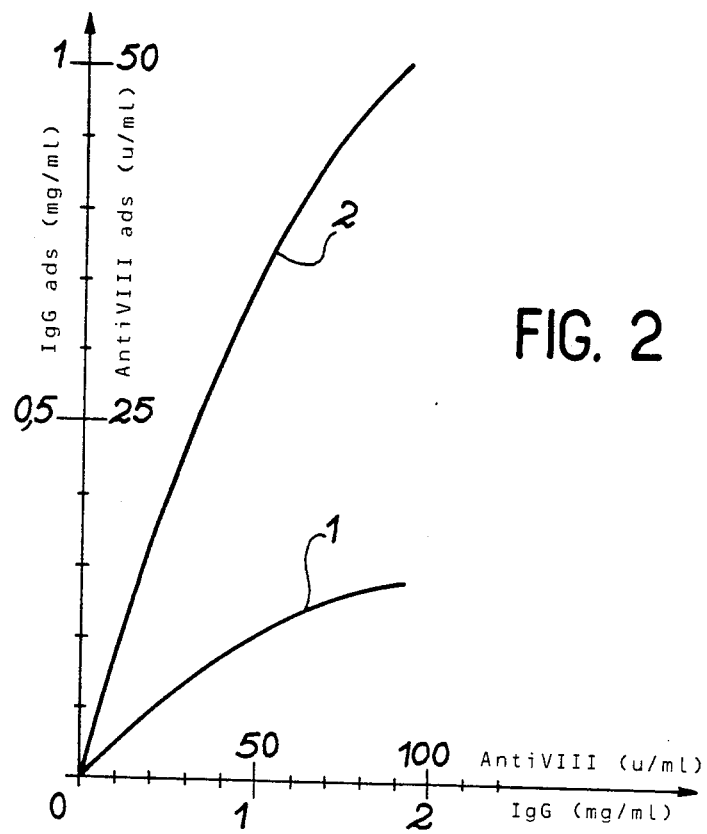
FIGS. 2 and 3, the adsorption isotherms of immunoglobulins IgG and antiVIII:C antibodies on different supports.
Figure 3:
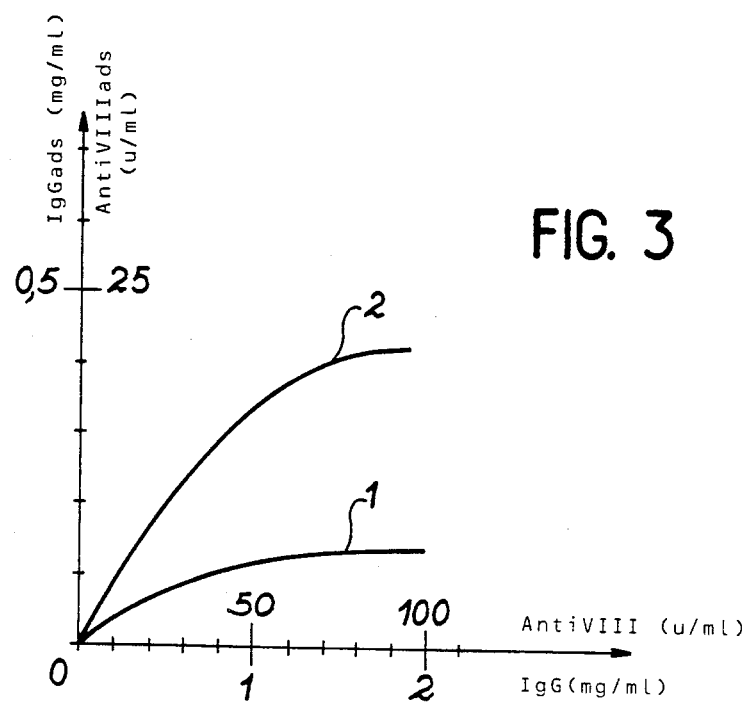

FIGS. 2 and 3 show the adsorption isotherms of IgG and antiVIII:C corresponding to the supports of examples 1, 2 and 7. Curves 1 correspond to the adsorption of IgG and on the abscissa are plotted the IgG concentrations in in mg/ml before adsorption and on the ordinate the IgG concentrations in mg/ml adsorbed on the support. Curves 2 correspond to the isothermic adsorption of antiVIII:C and on the abscissa are plotted the antiVIII:C concentrations in u/ml before adsorption and on the ordinate the antiVIII:C concentrations in u/ml which have been adsorbed. The scales taking account of the specific activity of IgG$_H$ permits a direct comparison of the two isotherm types.

On the basis of these curves, it is possible to determine the value $S_1$ of the relationship of the slope of the adsorption isotherm (2) relative to the antiVIII:C with the slope of the adsorption isotherm (I) relative to IgG and the value $S_2$ of the relationship between the adsorption values at the plateau for the two aforementioned isotherms. When the support has a zero selectivity for antiVIII:C, the two types of adsorption isotherms are superimposed and $S_1$ and $S_2$ are close to one. However, when the selectivity is high, $S_1$ and $S_2$ have high values.

In the attached table, the values of $S_1$ and/or $S_2$ obtained during the adsorption tests have been transferred to the supports of examples 1 to 8. It is possible to see that the best selectivities are obtained with the supports of examples 4, 1, 5 and 8 respectively corresponding to the fixing of hydroxyproline, glutamic acid, threonine and lysine on chlorosulphonated polystyrene. In the case of the support of example 1, 60% of the antiVIII:C antibodies are adsorbed, whereas only 16% of the IgG are adsorbed, which represents a good selectivity. Good results are also obtained with the supports of examples 2 and 3.

However, in the case of example 6, no selectivity is obtained, because the value of $S_1$ is below 1, which does not permit the selective adsorption of the antiVIII:C antibody.

Thus, methyl glutamate does not have selectivity when the glutamic acid has a very good selectivity, which shows that better results are obtained when the radical $R_1$ of Y has an acid function. In the same way, the results obtained with proline are less satisfactory than those obtained with hydroxyproline, because in the case of proline the radical $R_1$ has a OH function.

Thus, the nature of the fixed amino acid has a preponderant influence on the result obtained.

EXAMPLE 10 polystyrene support to which are only fixed —SO$_3$Na groups.

As in example 1 (a) chlorosulphanated polystyrene containing 4 meq/g of —SO$_2$Cl groups is prepared and the chlorosulphonyl functions are then hydrolyzed using a 2 M NaOH soda solution at a temperature of 60° C. The powder, which has undergone chlorosulphonation, is submerged in this soda solution for 24 hours, so that all the —SO$_2$Cl functions are transformed into —So$_3$Na groups.

The thus prepared support is conditioned and washed as in example 9(a) and with said support are performed adsorption tests for the antiVIII:C antibodies present in the plasma of a hemophiliac under the same conditions as in example 9.

On the basis of adsorption isotherms obtained under the same conditions as those of example 9, a determination takes place of the values of $S_1$ and $S_2$ and it is found that $S_1=3.2$ and $S_2=2.7$. Thus, said support also has interesting properties for carrying out the selective adsorption of antiVIII:C antibodies.

Figure 4:
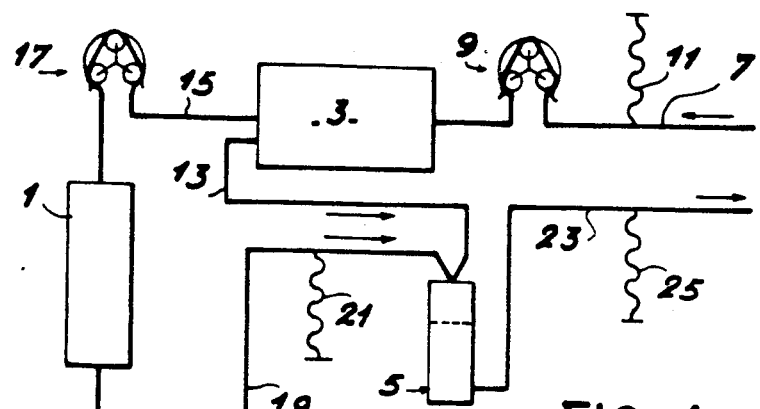
FIG. 4, diagrammatically a column plasma purifier for performing the inventive process.
Figure 5:
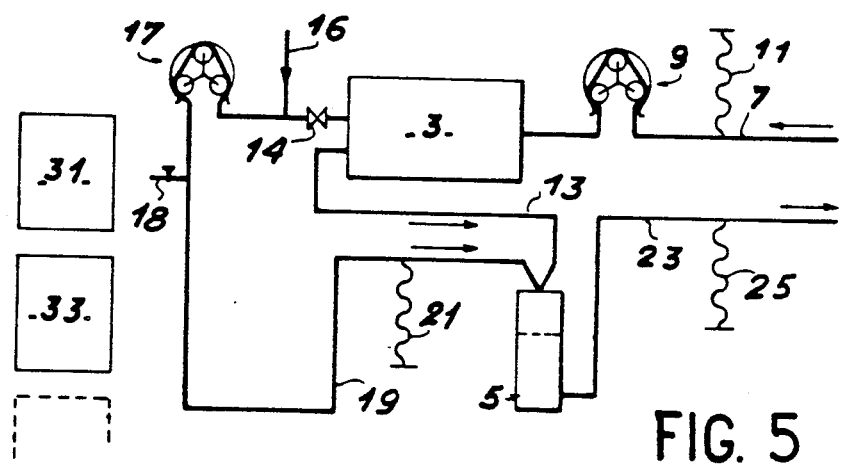
FIG. 5, diagrammatically another plasma purifier type.

The supports according to the invention can be used for the purification of the blood plasma in purifies shown in FIGS. 4 and 5.

In FIG. 4, which illustrates the continuous purification of the blood plasma, it can be seen that the purifier comprises a column 1 containing the adsorbant support according to the invention, a cell separator 3 for isolating the blood plasma from the blood to be purified and a collector 5 into which are introduced on the one hand the separated cells of the blood to be treated (at three) and on the other hand the purified plasma.

In said installation, a first pipe 7 provided with a pump 9 and a pressure measuring means 11 is used for introducing the blood from the patient into the cell separator 3, where the cells are discharged by pipe 13 to collector 5, whilst the plasma is directed by pipe 15, provided with a pump 17, into the column 1 containing the adsorbant support according to the invention. On leaving column 1, the purified plasma is discharge by pipe 19 equipped with a pressure measuring means 21 into collector 5, which also constitutes a safety system to prevent the presence of bubbles in the thus reconstituted blood. The latter is discharged by pipe 23 having pressure measuring means 25 into the patient's circulatory system. Thus, pipes 7 and 23, which are respectively used for introducing the blood into the apparatus and its return to the circulatory system are tapped into the patient's vein.

FIG. 5 shows a purifier in which the purification of the plasma takes place discontinuously, whilst the system is continuously traversed by the patient's blood. Most of the components of the purifier of FIG. 4 again appear and carry the same references. In this case, the blood plasma form the cell separator 3 is discontinuously purified in containers 31 and 33 containing the adsorbant support according to the invention. In this case, the plasma circulated by pump 17 can be extracted from the circuit and introduced into container 31 by draw-off valve 18. Following purification in container 31, the purified plasma is reintroduced upstream of pump 17 by pipe 16, whilst valve 14 is closed.

The supports according to the invention can also be used for purifying the VIII:C factor. In this case, on the support according to the invention the antiVIII:C antibodies are firstly adsorbed by contacting the support with the plasma containing said antibodies. The support, to which the antiVIII:C antibodies have been fixed, can then be used for purifying the VIII:C factor by contacting the latter with a liquid containing the VIII:C factor.

TABLE

| Fixed amino acid | SO$_3$Na meq/g | SO$_2$Y* meq/g | R$^1$ | R$^2$ | S$_1$ | S$_2$ |
|---|---|---|---|---|---|---|
| glutamic acid (ex. 1) | 3.2 | 0.8 | $-(CH_2)_2COOH$ | H | 4.3 | 4.2 |
| Alanine (ex. 2) | 1.3 | 2.7 | —CH$_3$ | H | 3.2 | 3.1 |
| Phenyl alanine (ex. 3) | 2.9 | 1.1 | —CH$_2$—C$_6$H$_5$ | H | 3.0 | |
| Hydroxyproline (ex. 4) | 1.8 | 2.2 | NH—(pyrrolidine with OH) | H | 4.5 | 4.5 |
| threonine (ex. 5) | 3 | 1 | —CHOH—CH$_3$ | H | 3.7 | 3.1 |
| methyl glutamate (ex. 6) | 2.7 | 1.3 | $-(CH_2)_2COOCH_3$ | H | 0.34 | |
| proline (ex. 7) | 2.3 | 1.7 | HN (pyrrolidine) | H | 2.2 | |
| Lysine (ex. 8) | 3.2 | 0.8 | $-(CH_2)_4NH_2$ | H | 2.6 | |

*Y = NH—CH—R$^1$
        |
        COOR$^2$

What is claimed is:

1. A process for the separation of antiVIII:C antibodies present in a liquid, which comprises:
   (a) contacting said liquid with a solid support constituted by a polymer or copolymer having substitutable groups in its chain and whereof at least part is substituted by
   groups of formula —(SO$_3$)$_x$M, in which M represents a metal which does not react with the liquid and x represent the valency of M,
   groups of formula —SO$_2$Y, or
   groups of formula —COY, in which Y represents a radical obtained by removing a hydrogen atom from the amino function of an α-amino acid other than arginine or an α-amino acid derivative other than arginine having an affinity for antiVIII:C antibodies and a selectivity for antiVIII:C antibodies with respect to other immunoglobulins and
   (b) separating the liquid from the support on which have been adsorbed the antiVIII:C antibodies.

2. A process according to claim 1, wherein radical Y is in accordance with the formula:

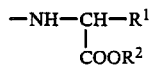

in which $R^1$ represents the side chain of an α-amino acid and $R^2$ a hydrogen atom or an alkyl radical, the radical $R^1$ having at least one function chosen from among the functions COOH, —NH$_2$, —OH and —SH.

3. A process according to claim 1, wherein the radical Y is obtained by removing a hydrogen atom from the amino function of the glutamic acid.

4. A process according to claim 1, wherein the radical Y is obtained by removing a hydrogen atom from the amino function of hydroxyproline.

5. A process according to claim 1, wherein the radical Y is obtained by removing a hydrogen atom from the amino function of threonine.

6. A process according to claim 1, wherein the radical Y is obtained by removing a hydrogen atom from the amino function of an amino acid chosen from among alanine, phenylalanine and lysine.

7. A process according to any one of the claims 1 to 6, wherein said support is constituted by polystyrene or a styrene copolymer to which are fixed groups of formula —SO$_2$Y, in which Y has the meaning given in any one of the the claims 1 to 6 and groups of formula —(SO$_3$)$_x$M, in which M represents a metal which does not react with the liquid and x represents the valency of the metal M.

8. A process according to claim 7, wherein the styrene copolymer is constituted by a styrene-grafted, chlorosulphonation-resistant polymer.

9. A process according to claim 8, wherein the chlorosulphonation-resistant polymer is chosen from among polyolefins, fluorinated polymers and polyvinylchloride.

10. A process according to any one of the claims 1 to 6, wherein said support is constituted by a polysaccharide, to which are fixed groups of formula —COY, in which Y has the meaning given in any one of the claims 1 to 6, and groups of formula CH$_2$CONHR$^4$—SO$_3$R$^5$, in which R$^4$ represents an alkyl, aryl or alkylaryl which may or may not be substituted and R$^5$ represents a hydrogen atom or a metal not reacting with the liquid.

11. A process according to claim 10, wherein the polysaccharide is a polydextran.

12. A process according to any one of the claims 1 to 11 wherein the liquid is blood plasma.

13. An application of the process according to any one of the claims 1 to 11, to the ex-vivo purification of the blood of a patient suffering from type A hemophilia.

* * * * *